United States Patent [19]

Rubinstein

[11] Patent Number: 5,709,992
[45] Date of Patent: Jan. 20, 1998

[54] METHOD FOR DISINFECTING RED BLOOD CELLS

[76] Inventor: Alan L Rubinstein, 100 S. Doheny Dr. #301, Los Angeles, Calif. 90048

[21] Appl. No.: 506,589

[22] Filed: Jul. 25, 1995

Related U.S. Application Data

[63] Continuation-in-part of Ser. No. 291,442, Aug. 17, 1994, abandoned.

[51] Int. Cl.$^6$ .................................................. A01N 1/02
[52] U.S. Cl. ................................................................. 435/2
[58] Field of Search ................................................. 435/2

[56] References Cited

U.S. PATENT DOCUMENTS

| | | | |
|---|---|---|---|
| 5,019,402 | 5/1991 | Kross et al. | 424/665 |
| 5,185,371 | 2/1993 | Rubinstein | 422/28 |
| 5,281,392 | 1/1994 | Rubinstein | 422/28 |

Primary Examiner—Johann Richter
Assistant Examiner—Ebenezer Sackey
Attorney, Agent, or Firm—Ostrolenk, Faber, Gerb & Soffen, LLP

[57] ABSTRACT

A process to disinfect units of red blood cells by adding an oxidizing agent, for instance ozone generating compounds, in solution to a unit of RBC's (RBC's) or compounds generating $ClO_2$, the RBC reducing enzymes such as cytochrome $b_5$ reductase will prevent or reverse oxidative changes, however, the viruses or other microorganisms do not have such enzymes. By adding RBC reducing enzymes to the RBC's before sterilization, the RBC's are further protected from the oxidizing sterilizing solution. The RBC's can be put in storage medium containing a reducing agent. The oxidizing agent may be generated from activated ceramic particles which will generate $O_3$ (ozone) in solution. This is a convenient and economic method of RBC sterilization. The activated ceramic particles generating $O_3$ in solution may also be added to units of whole blood.

20 Claims, No Drawings

METHOD FOR DISINFECTING RED BLOOD CELLS

RELATED APPLICATIONS

This is a continuation-in-part of U.S. patent application Ser. No. 08/291,442, filed Aug. 17, 1994 now abandoned.

BACKGROUND

1. Field of the Invention

The present invention relates generally to processing and disinfecting human blood products. More particularly, this invention relates to disinfecting red blood cells (RBC's), so that they may be used safely and effectively for diagnostic, therapeutic or research purposes.

2. Description of the Related Art

Blood products from human and animal donors are widely used for therapeutic, diagnostic and experimental purposes. A persistent problem associated with using blood products from human and animal donors is that these products are subject to contamination by blood-borne viruses and other micro-organisms such as bacteria.

Of particular threat are viruses that appear to cause various forms of hepatitis, including the hepatitis B virus; the non-A, non-B hepatitis virus or viruses commonly called hepatitis C. Others of interest are cytomegalovirus and Epstein-Barr virus. Units of RBC's may also have bacterial contamination, for instance yersinia enterocolitica.

Viruses linked with the incurable and often fatal disease known as acquired immune deficiency syndrome or "AIDS" are caused by a retrovirus or group of retroviruses previously denominated "HTLV-III" and other HTLV types—and more currently "HIV," "HIV-1" and "HIV-2." The most common cause of AIDS is thought to be HTLV-III, now usually called HIV-1. Several subtypes of HIV-1 and HIV-2 have-been described including group O. Because HIV is so rapidly mutating, current screening tests may not detect no emerging virulent forms. This invention describes an economical, streamlined procedure to assure viral inactivation or disinfection even if screening tests are inadequate.

Detection and isolation of such cytopathic retroviruses from patients with AIDS, and certain members of groups that are at high risk for AIDS, have been frequently reported. One such early report appears in *Science* 224:500–03 1984). Such findings are corroborated by P. S. Savin, et al., in an article entitled "Human T-Lymphotrophic Retroviruses in Adult T-Cell Leukemia-Lymphoma and Acquired Immune Deficiency Syndrome," *J. Clinical Immunol.* 4:415–23 (1984). Yet another report is by F. Wong-Staal and R. C. Gallo "Human T-Lymphotrophic Retroviruses," *Nature* 317:395–402 (1985).

The threat of hepatitis, AIDS, and bacterial transmission through transfusion and administration of blood products is not limited to blood cells but extends to the administration of plasma and plasma fractions such as Factor VIII concentrates, Factor IX concentrates, gamma globulin, and antithrombin III.

Disinfecting whole blood and blood products, including red blood cells, plasma and plasma fractions with disinfectants strong enough to significantly inactivate viruses, bacteria and other organisms has generally been discounted because they have been believed to damage cellular blood constituents or inactivate plasma and plasma protein factions. Additionally, the presence of any residual disinfectant in the blood product to be transfused could be hazardous to the recipient of the transfusion.

One disinfectant in use for blood products is beta-propiolactone. Beta-propiolactone, however, is a known carcinogen and hence potentially very dangerous. To the extent that significant residual amounts of this material may remain in the blood product which is actually transfused, the use of propiolactone represents a potential hazard.

U.S. Pat. No. 4,833,165 relates to using as little as 0.1% formaldehyde and/or phenol to inactivate HTLV-III in blood. However, recently available data and information indicate that red blood cells treated with as little as 0.02% formaldehyde and 0.01% phenol are not viable and not suitable for transfusion. In fact, formaldehyde is used in pathology to "fix tissue" for examination.

Applicant's former applications disclose the utility of normal saline and other isotonic solutions of chlorine dioxide for sterilizing certain blood products, specifically units of RBCs and tissue products. Quite unexpectedly, chlorine dioxide, a disinfectant strong enough to inactivate blood born viruses and microorganisms, can be utilized to disinfect cellular blood products without destroying the vitality and integrity of the cells. This invention further improves the process of disinfecting units of RBCs by allowing greater concentrations of oxidizing agent for disinfection.

SUMMARY OF THE DISCLOSURE

It is the object of this invention to provide compositions and methods to disinfect units of red blood cells (RBC's) for their safe and effective use. The invention is based upon the surprising and unexpected discovery that oxidizing compounds, which heretofore have been discounted as blood product disinfectants may be used for disinfecting red blood cells, without a resulting loss in red blood cell viability. This is because RBC reducing enzymes, e.g., cytochrome $b_5$ reductase, glutathione reductase, glutathione peroxidase and the NADH system as well as the superoxide desmutases and catalase and other reducing systems will prevent or reduce or reverse oxidation by the oxidizing sterilizing solution. For instance, the oxidized form of Hb, i.e., methemoglobin will be reduced back to Hb. This invention demonstrates that by adding the RBC reducing enzymes to the unit of RBC's before the sterilizing oxidizing solution, there is further protection of the RBC's from oxidation. The RBC reducing enzymes may also be added to the sterilizing solution without reducing the strength of the oxidizing agent. The viruses and other microorganisms do not have the RBC reducing enzyme systems and thus will not be protected. Following contact with the oxidizing sterilizing solution the unit of RBC's may be washed with an isotonic solution containing a reducing agent. Additionally, oxidizing compounds can be used to disinfect plasma proteins such as Factor VIII, gamma globulins, more specifically IV IgG, Factor IX, and antithrombin III without denaturing the protein or otherwise diminishing the protein physiological activity.

The present invention is based upon the discovery that whole blood and units of red blood cells (RBC's) can be disinfected by providing disinfectant compositions of an oxidizing compound and a diluent, and then mixing whole blood or blood product (RBCs) with the disinfecting compositions for a length of time sufficient to inactivate any bacteria and virus present in the blood or blood product. After the blood or blood product is disinfected, the oxidizing compound is separated from the disinfecting composition, thereby providing blood or blood product which is safe and effective for therapeutic or diagnostic use.

For disinfecting red blood cells, diluents are aqueous solutions of an isotonic effective concentration of oxidizing solute. More particularly, these diluents include solute which, when dissolved in water at an isotonic effective concentration form solutions which are isotonic with blood. Surprisingly, processes utilizing isotonic solutions of an oxidizing compound will not only disinfect red blood cells but will do so without damage to red blood cells. This is because of the reducing enzyme systems of RBC's. With respect to plasma and plasma protein fractions, the disinfectant composition need not be isotonic with respect to blood and water or sterile water is a suitable diluent for such compositions. Accordingly, disinfectant compositions consisting of an oxidizing compound in sterile distilled water will effectively disinfect plasma and plasma protein fractions without a resulting loss in physiological activity of the plasma.

This invention may be practiced using economical procedures which are easily adapted to existing techniques for handling blood and blood products including red blood cells and plasma. Moreover, this invention can be implemented even while blood is in a collection bag. Typically, procedures for disinfecting blood and blood products include washing blood or blood products in a disinfecting composition and then separating the blood or blood product from the disinfecting composition.

The concentration of oxidizing compound in the disinfectant composition and the time required to effectively inactivate any harmful substance present in the blood are dependent upon the disinfectant strength. Suitable concentrations and disinfecting times will become evident in the more detailed description of the invention and the exemplary embodiments.

Separating the oxidizing compound from the blood is accomplished by washing the disinfectant composition and blood in a suitable medium until the disinfectant is reduced to a safe or insignificant level. Preferably the medium is the same as that used to disinfect the red blood cells, plasma or plasma product.

Further objects, features and advantages of the present invention will become apparent to those skilled in the art from a consideration of the following detailed description.

DETAILED DESCRIPTION OF THE PREFERRED EMBODIMENT

The present invention involves the effective and safe disinfection of red blood cells and blood products. The invention has wide application to all blood products such as whole blood for transfusion, blood cells, blood plasma and blood plasma proteins. Since whole blood is rarely used, the present invention is more particularly directed to processes for disinfecting red blood cells and blood plasma.

In accordance with the preferred method for disinfecting blood products, a method is provided in which viruses and bacteria including the HIV viruses, in red blood cells and blood products may be used for therapeutic or diagnostic purposes in a safe and effective manner. The invention is based upon the unexpected discovery that disinfectant compositions of oxidizing compounds which are substantially isotonic with blood do not lyse red blood cells or cause harm to blood products. Moreover, disinfectant compositions of oxidizing compounds which are not isotonic with respect to blood, and which until now have not been considered for use with blood products, can be used to disinfect plasma and plasma proteins without denaturing the protein or otherwise causing a substantial loss in physiological activity.

In accordance with the present invention, methods for disinfecting red blood cells or blood products are provided which include the steps of providing a disinfectant composition of a disinfecting concentration of oxidizing compound and a diluent and then mixing whole blood or blood product with the disinfecting composition for a length of time sufficient to inactivate any bacteria and virus present in the blood or blood product. After the blood or blood product is disinfected, the oxidizing compound is separated from the disinfecting composition, providing blood or blood product which is safe and effective for therapeutic or diagnostic use.

Suitable oxidizing compounds having utility in the practice of the present invention include but are not limited to chlorine dioxide, sodium tetraborate decahydrate, sodium perborate tetrahydrate, potassium permanganate, sodium nitrate, sodium persulfate, calcium hypochlorite, potassium chlorate, benzoyl peroxide, potassium nitrate and sodium hypochlorite. When chlorine dioxide is the oxidizing compound utilized in disinfecting blood or blood products according to the present invention, the chlorine dioxide is preferably generated in situ by the reaction of sodium chlorite and a Brönsted acid or alternative chlorine dioxide generating reagents. The preferred oxidizing agent is the sodium-chlorate plus lactic acid generation of $ClO_2$.

As described below, the above-identified oxidizing compounds will effectively disinfect blood and blood products without substantial loss of physiological activity. It is also contemplated as being within the teachings of the present invention to disinfect blood or blood products with oxidizing compounds having sufficient oxidizing properties to inactivate viruses and bacteria. Thus, a wide variety of oxidizing compounds are available for disinfecting blood and blood products including chlorine, chloride of lime, inorganic oxo compounds, hypochlorous acid, chlorous acid and salts thereof, perchloric acid, potassium peroxodisulphate, sodium peroxide, barium peroxide, urea peroxohydrate, and alkali perborates. It is understood that this invention covers the use of all oxidizing agents.

Exemplary disinfectant composition used for disinfecting whole blood or red blood cells according to the present invention include diluents in the form of aqueous solutions having an isotonic effective concentration of solute. For purposes of the present invention, isotonic effective concentrations are a concentration of suitable solute which renders the disinfectant composition substantially isotonic with blood. Those skilled in the art will appreciate that when the disinfectant composition includes sufficient oxidizing compound to contribute to the tonicity of the disinfectant composition, the isotonic effective concentration of any given solute is less than that required when the oxidizing compound does not significantly contribute to the tonicity of the disinfecting composition. Thus, when a disinfectant composition consists of less than 0.001 wt % sodium chlorite and less than 0.005 wt % Brönsted acid reacted to form chlorine dioxide, there is very little if any osmotic pressure contributed by oxidizing compound. In order to have an isotonic disinfectant composition in this case, the diluent itself is isotonic and includes solute sufficient to render the diluent isotonic. When RBC reducing enzymes are added to the sterilizing solution or to the unit of RBCs, suitable adjustments to insure approximate isotonicity of the sterilizing solutions and the unit of RBCs must be made.

On the other hand, when the disinfectant composition includes, for example, an aqueous solution of about 0.25 wt % sodium chlorite and about 0.2 wt % Brönsted acid which, react to form an oxidizing compound, the aqueous diluent requires less solute to render the disinfectant composition isotonic or when RBC reducing enzymes or enzyme systems are added. In this case, the oxidizing compound provides some degree of tonicity to the aqueous disinfectant composition and the diluent can include less solute, for example 0.45 wt % sodium chloride. When disinfecting cellular blood products such as red blood cells, in accordance with the teachings of the present invention, the controlling factor is that the disinfectant composition have a tonicity which is sufficiently close to that of blood so that hemolysis is prevented.

In accordance with the present invention, suitable diluent solutes include any of a number of compounds used in the preparation of isotonic solutions. Exemplary solutes include but are not limited to sugars such as dextrose and glucose, polysaccharides such as dextran, albumin, and salts of alkali earth metals including sodium chloride, potassium chloride, and potassium bromide. Combinations of solutes known for their utility in storing physiological cells and tissue are also suitable and include such combinations as citrate-phosphate-dextrose, citrate-phosphate-dextrose-adenine, and saline-mannitol-dextrose-adenine. As described in greater detail below, the presence of at least one solute in the dilute in the form of a sugar is preferred because sugar contributes to the reduction of any methemoglobin, oxidized hemoglobulin, formed during the disinfecting process.

Advantageously, diluents having utility in the practice of the present invention for their isotonic characteristics can be combined. Combining diluents is particularly suitable when disinfecting red blood cells because commercial collective units of red blood cells are frequently stored in isotonic solutions containing anti-coagulant, such as ACD (acid-citrate-dextrose), CPD (citrate-phosphate-dextrose), CPD-A (CPD-adenine) and Adsol (adenine, dextrose, saline and mannitol). Thus, when disinfecting collective units of red blood cells stored in isotonic solutions of anti-coagulant, the disinfectant composition may be prepared in a different isotonic diluent, e.g., normal saline, and combined with the anti-coagulant solution.

Further in accordance with the present invention, processes for disinfecting plasma or plasma products, such as plasma protein fractions, optionally utilize disinfecting compositions having no solute and in which the diluent is sterile water, water, distilled water or sterile and distilled water. Because plasma and plasma products do not contain tissue or other forms of cellular material, there is no compelling need to have an isotonic medium for maintaining cellular osmotic pressure.

Providing a disinfectant composition of oxidizing agent and diluent is accomplished by simply combining the selected oxidizing agent and diluent and gently stirring. In the case of the in situ formation of oxidizing agent, such as chlorine dioxide, the reagents are combined and then allowed to react for a short time to form the chlorine dioxide.

Mixing a disinfectant composition with blood or blood products can be performed by simply combining the red blood cells or blood product and disinfectant composition in a suitable container with light agitation to assure sufficient interaction between the red blood cells and disinfectant composition. Suitable containers include but are not limited to blood collection bags and blood storage apparatus. It is preferable, however, to utilize automated cell washing equipment known in the art and available from a variety of sources including Cobe.

In accordance with the present invention disinfecting effective concentrations of oxidizing compound and sufficient periods of time for disinfecting blood and blood products are primarily dependent upon the choice of oxidizing compound. It can also be appreciated that useful concentrations of oxidizing compound and periods of time for disinfecting are interdependent. Thus, oxidizing compound concentrations can be varied and a relatively small concentration of oxidizing agent can be a disinfecting effective concentration when mixed with red blood cells or blood products for longer lengths of time. Conversely, when relatively larger concentrations of oxidizing agent are utilized in disinfectant compositions, the period of time sufficient to disinfect blood or blood products is less.

Suitable periods of time for disinfecting will become apparent when considering the detailed examples which follow this discussion. It is understood that disinfecting effective periods of time may be adjusted in accordance with known principles of chemistry to accommodate treatment of the whole blood or blood product while it is refrigerated or even heated. Generally, disinfecting times will range from as low as 30 seconds to as high as 30 minutes. The preferred times, however, are in the range of 2 minutes to 10 minutes. Care must be taken in using lower or higher temperatures to avoid damage to cells, blood or protein products from the exposure itself—or from the combination of conditions of temperature and disinfecting composition. Generally, room temperature conditions can be utilized, however, some products may require lower disinfecting temperatures.

Finally, the separating step includes thoroughly washing the disinfected blood or blood products with washing diluent for a length of time sufficient to remove substantially enough oxidizing compound to provide safe and physiologically active disinfected blood or blood products for therapeutic or diagnostic use. For separating red blood cells from the disinfectant, the disinfectant composition and red blood cell mixture is typically centrifuged while repeatedly adding volumes of washing diluent. Additionally, this separating step preferably further includes washing red blood cells in automated cell washing equipment such as that described above for mixing units of red blood cells with a disinfectant composition. It should be noted that the use of cell washing equipment is not necessary when no or negligible residual disinfectant remains after centrifuging. The whole procedure may be done manually without a cell washer and just with a centrifuge.

When separating disinfected red blood cells or disinfected whole blood in accordance with the present invention, washing diluent is preferably aqueous solutions which are substantially isotonic with blood. Such an aqueous solution can be the same diluent and solute utilized in the disinfectant composition. The term "substantially isotonic" is used to indicate that the disinfectant solution need not have an osmolality equal to that of blood but can be approximate to that of blood. Preferably, the washing diluent is a substantially isotonic aqueous solution which may include a sugar as a solute as well as a solution containing a reducing agent, e.g., ascorbate. Furthermore, the storage solution may also contain a reducing agent, i.e., ascorbate. As mentioned above and discussed in more detail below, the presence of at least one sugar in the washing diluent contributes to reducing any methemoglobin, formed during the disinfecting process to hemoglobin.

When separating disinfectant plasma or disinfected plasma products such as plasma protein fractions in accordance with the present invention, washing diluent need not include solute and can be water, sterile water, distilled water or distilled and sterile water. However, it is within the scope of the present invention to utilize washing diluent which is substantially isotonic with blood for washing plasma and plasma products. Additionally, when separating disinfected plasma protein fractions, the separating step preferably includes precipitating the plasma protein fractions as known in the art. For example, plasma proteins and plasma protein concentrates such as Factor VII, Factor IX, antithrombin III, fibrinogen and immune globulins can be disinfected and then precipitated by contacting the disinfected plasma protein with an aqueous solution of about 80 wt % ammonium sulfate or similar precipitating agent.

Next, the disinfected and precipitated plasma proteins or plasma are resuspended in an aqueous solution which is preferably a solution which is isotonic with blood. Then, exhaustively dialyzing the resuspended plasma proteins or plasma against a relatively large volume of aqueous solution which is also preferably isotonic with blood reduces the concentration of oxidizing compound and precipitating agent. Alternatively, the dialyzing step may be replaced by high speed centrifugation using conventional techniques for separating proteins.

After the blood or blood product in the form of whole blood, red blood cells, plasma and plasma protein fractions is disinfected and separated from the oxidizing compound, it is preferably stored in an aqueous solution which incorporates a sugar. This is a particularly advantageous step when the disinfected blood product is red blood cells because the presence of sugar has been shown to contribute to the reduction of the small amount of methemoglobin to hemoglobin, which can form from the oxidation of hemoglobin by the disinfecting composition. Preferably, the storage medium can contain a reducing agent. Such reducing agent may be a relatively strong reducing agent, e.g., sodium ascorbate, or a weaker reducing agent, e.g., mannitol.

Accordingly, by storing red blood cells, disinfected according to the teachings of the present invention, in storage solutions such as adenine and saline (AS-3), which are approximately isotonic, or adenine-glucose-saline-mannitol (SAGM) and ascorbate the oxidized hemoglobin is converted back to hemoglobin by enzymes indigenous to normal red blood cells, the NADH-diaphorase I, cytochrome $b_5$ and NADPH-linked methemoglobin-reducing system enzymes. It is preferred that there be present some dextrose. As mentioned above, the practice of using sugar containing diluents in the disinfectant composition during the mixing and separating steps of the present invention additionally reduces the amount of methemoglobin formed during the disinfecting process. The presence of a sugar at a concentration of as low as 0.1 wt % in the diluent and washing solution is effective. Thus, normal saline which incorporates 0.1 wt % dextrose is effective in reducing the amount of methemoglobin. Moreover, diluents and washing solutions which are rendered isotonic by the amount of sugar present such as 5 wt % dextrose can also be utilized.

It is contemplated as being within the scope of the present invention to repeat the mixing and separating steps. For example, after a unit of red blood cells is mixed with a disinfectant composition and separated from the oxidizing compound, the same unit can be repeatedly mixed with fresh isotonic disinfecting solutions. When minimal disinfecting times are used for each cycle, this technique increases the inactivation of any viruses or bacteria present.

A preferred embodiment of this invention is the use of activated ceramic particles which upon contact with $H_2O$ release $O_3$ (ozone) in solution. These activated ceramic particles may be added to whole blood and then filtered out when the whole blood unit is separated into plasma and red blood cells. This is a novel invention since now the $O_3$ can be generated efficiently in solution without the need for gaseous generation.

Practicing this invention procedure is practical, useful, streamlined and economical. Its advantages particularly include eliminating transmission of viruses and microorganisms in unit of red blood cells.

All of the foregoing operational principles and advantages of the present invention will be more fully appreciated upon consideration of the following detailed examples.

EXAMPLE 1

The following example demonstrated that disinfecting solutions of chlorine dioxide formed in situ results in the formation of only small amounts of methemoglobin.

Thirty mL of fresh peripheral blood from a healthy donor was collected in a heparinized syringe. The blood was then centrifuged at 2,000 rpm to separate the red blood cells.

A disinfectant composition was prepared using the following procedure:

Three mL of a 15% aqueous lactic acid solution was added to 30 mL of aqueous normal saline. Then 3 mL of a 2.73% aqueous sodium chlorite solution was added to the lactic acid in normal saline solution. The disinfectant composition was allowed to sit at room temperature for 70 minutes and then it was diluted 1:10 in normal saline solution. The resulting disinfectant composition is 0.125% lactic acid and 0.023% sodium chlorite and generates chlorine dioxide.

A 3 mL aliquot of packed red blood cells which was separated from the whole blood during the centrifugation was mixed with 3 mL of the disinfectant composition. The red blood cell and disinfectant composition mixture was allowed to incubate at room temperature for 5 minutes.

A second 3 mL aliquot of packed red blood cells was mixed with another 3 mL of the disinfectant composition and allowed to incubate at room temperature for 10 minutes.

A third 3 mL aliquot of packed red blood cells was mixed with 3 mL of normal saline solution and utilized as a control.

Following the incubation step, the red blood cells were separated from the two disinfecting solutions and the control solution by centrifuging and then washing four times with equal volume of normal saline solution.

All of the samples were then sent to a commercial laboratory for methemoglobin analyses which were determined as follows:

Control sample 0.6% (within normal range of 3%)

Disinfected 5 min.: 6.6%

Disinfected 10 min: 6.2%

The above results probably are not physiologically significant. Moreover, the difference between the 5 minutes and 10 minute exposure is negligible.

EXAMPLE 2

An aliquot of RBC's are washed in 0.9% NaCl and 0.2% dextrose. A highly concentrated approximate isotonic solution of RBC reducing enzymes consisting of cytochrome $b_5$ reductase, glutathione reductase and other reducing enzymes in concentration several times greater than their concentration in red cells are added to the RBCs. The RBC's are now washed in the sterilizing solution which is approximately isotonic containing the oxidizing agent, for instance, in this case, sodium chlorite and lactic/acid in concentrations of approximately 0.2% and 0.15% respectively. (That is the sterilizing solution (Alcide) is diluted, 1:100 with 5% dextrose.) Or activated ceramic particles which release ozone (03) upon contact with solution will furnish the oxidizing agent. These ozone releasing activated ceramic particles may also be added to units of whole blood. The RBC's are exposed for time periods of 1 minute to 4 minutes followed by washing with a solution containing a reducing agent of sodium ascorbate such that the solution is approximately isotonic. Followed by immersion in storage medium containing some reducing agent, e.g., ascorbate, however all solutions must be approximately isotonic. The final sterilized RBC's show no significant changes from the unsterilized controls.

One or more of the following RBC reducing enzymes or non-enzymes that are substances or compounds necessary for RBC reducing enzyme systems may be added to the unit of RBCs before the oxidizing sterilizing solution is added or with the sterilizing solution: Cytochrome b reductase, NADPH superoxide dismutase, glutathione, peroxidase, catalase, NADH, cytochrome $b_5$, NADH-flavin, NADPH methemoglobin reductase. It should be noted that these RBC enzymes and substances involved in RBC enzyme reduction are added to the unit of RBCs in a solution where their concentration is much greater than their concentration in the RBC, preferably several fold greater concentration. This facilitates the diffusion or entrance of the RBC reducing enzymes or compounds intracellular within the RBC.

The overall objective is to add substances which will slow or prevent oxidation of the RBC during sterilization but will not affect the strength of the oxidizing agent. This is done by adding the RBC reducing enzymes and substances participating in RBC reducing reactions. Such enzyme systems are not present in viruses or other harmful microorganisms. It should be noted, however, that just by adding reducing agents, for instance ascorbate, this will lessen the strength of the oxidizing sterilizing solution. However, adding the RBC reducing enzymes aforementioned will not affect the generation or strength of the oxidizing solution (sterilant). This is apparent from this example where the oxidizing agent is $ClO_2$ from sodium chlorite+acid. This is a very important feature of this invention and thus increases the time and concentration of the oxidizing sterilizing solution that the RBC can tolerate. This viral inactivation is increased without sacrificing RBC integrity and suitability for transfusion.

EXAMPLE 3

An oxidizing solution is prepared from activated ceramic particles, which are in the form of round beads approximately 1–2 mm in diameter. Upon contact with $H_2O$, the ionized electrons released give off ozone in solution. It is not necessary to provide exogenous gaseous ozone as the activated ceramic particles interact with the aqueous solution, e.g., normal saline or 0.9% dextrose solution to generate ozone in solution. The RBC reducing enzymes and compounds involved in RBC Hb reduction, for instance, glutathione, NADPH and NADH, as well as others, for instance: cytochrome, $b_5$ reductase, cytochrome $b_5$, dismutases and catalase, may be added before the sterilization or after the sterilization. Following the oxidative sterilization of the RBCs reducing solutions may be added to the sterilized unit of RBCs including ascorbate and others.

Example: To a blood collection bag activated ceramic particles are added which will generate electrons which will form ozone. The unit of whole blood is collected and separated into plasma and red blood cells. The ceramic particles are prevented from entering the RBC and plasma collection bags by filters that keep the ceramic particles in the original whole blood collection bag.

Example: An RBC collection bag containing, for instance, ADSOL® (aden, dextrose and saline and mannitol) contain imbedded in the part wherein the RBCs enter the unit, activated ceramic particles, such that when the RBCs enter that port, the ceramic particles are released and also enter the unit. The same mechanism for entry of the ceramic particles into a unit of whole blood may be used.

The unit of RBCs may contain also the RBC reducing enzymes and substances involved in RBC Hb reduction, e.g., NADH, NADPH, glutathione, cytochrome $b_5$.

A brief discussion of RBC reducing enzymes follows.

NADPH=nicotinamide-adenine, dinucleotide, phosphate. (Ref. Wintrobe's *Clinical Hematology*, Lee, et al., Editors Lea & Febiger, 1993.)

Most methemoglobin (oxidized Hb) in erythrocytes is reduced through the action of an enzyme, cytochrome $b_5$ methemoglobin reductase, which acts in the presence of two electron carriers, cytochrome $b_5$ and NADH.[160] Only a small amount of methemoglobin is reduced by all other pathways of methemoglobin reduction together (Table 5-9). These other pathways involve two compounds that cause the reduction of methemoglobin nonenzymatically, ascorbic acid and glutathione, as well as a second enzyme, NADPH-flavin reductase. Deficiency of cytochrome $b_5$ reductase, but not of NADPH-flavin reductase, is associated with methemoglobinemia, confirming that cytochrome $b_5$ reductase is the most important physiologic means of reducing methemoglobin.[198] In vitro evidence also confirms that cytochrome $b_5$ reductase is the rate-limiting factor in methemoglobin reduction.[174]

Cytochrome $b_5$ reductase has been referred to by several other names, including diaphorase I, DPNH dehydrogenase I, NADH dehydrogenase, NADH methemoglobin reductase, and NADH methemoglobin-ferrocyanide reductase. Early work by Gibson in the 1940s demonstrated a relationship between the reduction of methemoglobin and the metabolism of lactate to pyruvate, thus implying an important role for NADH.[152] Eventually, two methemoglobin-reducing enzymes were isolated. The NADH-dependent enzyme, which was absent from several patients with methemoglobinemia, has been shown to be a flavoprotein, with one mole of flavin-adenine dinucleotide (FAD) per mole of apoenzyme. Its molecular weight is approximately 34,000. Several investigators have identified the corresponding cDNA, and the gene has been localized to chromosome 22.[134,216] Most likely, erythrocyte cytochrome $b_5$ reductase and hepatic cytochrome $b_5$ reductase are the product of a single gene.

The reduction of methemoglobin by highly purified cytochrome $b_5$ reductase in the presence of NADH is extremely slow, implying that another factor is most likely required as an electron carrier. In vitro, this role can be filled by dyes or by ferrocyanide. In vivo, cytochrome $b_5$ acts as the intermediate electron carrier.[161] Erythrocyte cytochrome $b_5$ greatly accelerates reduction of methemoglobin by cytochrome $b_5$ reductase and can also serve as a substrate for hepatic microsomal cytochrome $b_5$ reductase. Congenital methemoglobinemia resulting from a deficiency in cytochrome $b_5$ has been described.[154] cDNA for human liver cytochrome $b_5$ has been cloned; it encodes a protein of 134 amino acids.[178]

Erythrocyte cytochrome $b_5$ probably results from proteolytic cleavage of the membrane-attached protein present in erythroid precursor microsomes, an event that then yields a soluble cytochrome $b_5$ protein.

The process by which cytochrome $b_5$ reductase and cytochrome $b_5$ reduce hemoglobin in the presence of NADH probably involves three steps. In the first, NADH binds to the FAD-reductase complex and, in the presence of hydrogen ion, the NAD is converted to NAD+, and the FAD becomes $FADH_2$. In the second step, cytochrome $b_5$_$Fe^{2+}$, and the $FADH_2$ reverts to FAD. Finally, methemoglobin forms a bimolecular complex with reduced cytochrome $b_5$ through electrostatic interactions between negatively charged groups around the cytochrome heme and positively charged groups around the heme moieties of methemoglobin. The reduction of methemoglobin then takes place and can be represented as follows:

$$HbFe^{3+} + Cytb_5Fe^{2+} \rightarrow HbFe^{2+} + Cytb_5Fe^{3+}$$

Of lesser physiologic importance is the enzyme system that depends on NADPH for its activity. It probably accounts for only about 5% of the methemoglobin-reducing activity of normal red cells (see Table 5-9), and its hereditary deficiency does not lead to methemoglobinemia.[129] The lack of physiologic activity may result from the absence of an intermediate electron carrier analogous to cytochrome $b_5$. If methylene blue is supplied as the carrier, however, the NADPH-dependent enzyme becomes highly effective in methemoglobin reduction. This property is used in the therapy of methemoglobinemia from various causes.

As molecular oxygen undergoes successive univalent reductions, a variety of reactive species are generated. These species constitute the oxidizing agents most likely to be responsible for the oxidative denaturation of hemoglobin, and they may damage other cellular components as well, especially lipid-containing elements such as the cell membrane.[139,149] A variety of mechanisms have evolved in respiring organisms to deal with these potential toxins, and some are found within the erythrocyte.

Once hydrogen peroxide is formed, two enzymes catalyze the decomposition of hydrogen peroxide in erythrocytes. The most important of these enzymes is glutathione (GSH) peroxidase,[144,155] which is a component of the following reaction:

$$H_2O_2 + 2\,GSH \xrightarrow{\text{GSH peroxidase}} 2\,H_2O + GSSG$$

The enzyme is effective at very low concentrations of peroxide ($Km = 1 \times 10^{-6} M$).[149]

Glutathione peroxidase is the major human selenoprotein,[151] which probably accounts for the antioxidant properties of selenium as a micronutrient.[150] Human cells grown in the absence of selenium express significantly reduced glutathione peroxidase activity, despite normal glutathione peroxidase mRNA and transcription levels. The gene for glutathione peroxidase appears to be on chromosome 3,[141] although two homologous genes also appear present in the human genome.[141,175] The importance of glutathione peroxidase is exemplified by the fact that a genetic defect in the enzyme may lead to a drug-sensitive hemolytic anemia.[180]

Catalase, a heme-enzyme, decomposes hydrogen peroxide to water and molecular oxygen.[212] It appears to be less important to the red cell than peroxidase, presumably because it is effective only when the peroxide concentration is relatively high.[164] Individuals with hereditary acatalasemia do not develop methemoglobinemia or hemolytic disease; an increase in glutathione peroxidase levels may compensate in part for the lack of catalase.[115] Some evidence suggests, however, that erythrocyte catalase may be important in preventing oxidant damage to somatic tissues.[116] Also, the level of catalase increases with physical conditioning, suggesting a physiologically significant role for erythrocyte catalase.[182]

Catalase consists of a tetramer composed of 60,000-dalton subunits, with four heme groups per tetramer. It is encoded by a gene on chromosome 11.[202] Catalase is a major component of erythrocyte band 4.5 seen on Coomassie-stained gels of erythroid membrane proteins, as the enzyme interacts with the membrane in a calcium- and pH-dependent manner.[121] Catalase also comprises a major reservoir of erythrocyte protein-bound NADPH. Each tetrameric molecule of erythrocyte catalase contains four molecules of tightly bound NADPH. Although not essential for enzymatic conversion of peroxide to oxygen, the NADPH appears to protect catalase from inactivation by peroxide.[167] For the purpose of this invention, those nonenzyme substances, e.g., NADPH, NADH, glutathione, cytochrome $b_5$ will be called "compounds" or "substances necessary for RBC reducing enzyme systems."

The most important product of the pentose phosphate pathway in erythrocytes is reduced nicotinamide-adenine dinucleotide phosphate (NADPH). The red cell lacks the reactions to use NADPH for energy; instead, NADPH, by serving as a cofactor in the reduction of oxidized glutathione (GSSG), is a major reducing agent in the cell and the ultimate source of protection against oxidative attack. The utilization of NADPH is the main stimulus to the utilization of glucose-6-phosphate by the pathway. Redox agents such as methylene blue, cysteine, ascorbate, and others[221,231] induce an up to 20-fold increase in pentose metabolism, presumably by bringing about oxidation of glutathione. This metabolic flexibility allows the red cell to respond to unexpected oxidant challenge.

A second function of the pentose pathway is the conversion of hexoses to pentoses. For the most part, the latter are recycled into the glycolytic pathway; however, D-ribose-5 phosphate may be used for nucleotide synthesis.

Having thus described preferred exemplary embodiments of the present invention, it should be noted by those skilled in the art that the disclosures herein are exemplary only and that alternative, adaptations and modifications may be made within the scope of the present invention. Accordingly, the present invention is not limited to the specific embodiments illustrated herein.

What is claimed:

1. A method to disinfect units of red blood cells (RBCs) consisting of adding a solution of red blood cell reducing enzymes selected from one or more of the following: cytochrome $b_5$ reductase and glutathione reductase, peroxidase, superoxide desmutase, glutathione peroxidase, and catalase; and an RBC reducing enzyme compound added to a unit of red blood cells and/or to the sterilizing solution or disinfectant.

2. A method as in claim 1 wherein the concentration of RBC reducing enzymes added is greater than their concentration in the RBC.

3. A method as in claim 1 wherein the sterilizing solution consists of an oxidizing agent.

4. A method as in claim 3, wherein the oxidizing agent is generated by activated ceramic particles.

5. A method as in claim 4, wherein the activated ceramic particles are in solution.

6. A method as in claim 5, wherein the activated ceramic particles upon contact with the aqueous solution forms ozone in solution.

7. A method as in claim 1 wherein the solution is approximately isotonic.

8. A method as in claim 1 whereby before and/or during the time of exposure to sterilant, one or more of the following RBC enzymes selected from the group consisting of superoxide desmutases, glutathione peroxidase, catalase, NADH, cytochrome b$_5$, NADH-flavin, glutathione, NADPH methemoglobin reductase and peroxidase is/are added to the unit of RBC.

9. A method as in claim 2 wherein the concentration of added enzyme or an RBC reducing enzyme compound(s) systems is several fold greater than the concentration in the red blood cells.

10. A method as in claim 1 wherein the unit of RBC's are exposed to an approximate isotonic solution of oxidizing agent containing RBC reducing enzymes and/or an RBC reducing enzyme compound(s).

11. A method as in claim 3 wherein the oxidizing agent is a solution of a chlorine dioxide liberating compound and an acid.

12. A method as in claim 3 wherein the sterilizing solution is washed out from the unit of red blood cells with an approximate isotonic solution containing a reducing agent.

13. A method as in claim 1 wherein the disinfected RBC's are stored in an approximate isotonic solution, preferably supplemented with an ascorbate reducing agent, whereby the resulting solution is approximately isotonic.

14. A method as in claim 7 wherein the solution contains dextrose.

15. A method as in claim 8 wherein the solution contains dextrose.

16. A method as in claim 3 wherein the oxidizing agent is formed from sodium chlorite and an acid.

17. A method as in claim 1, wherein the RBC reducing enzyme compound(s) is selected from the group consisting of NADH and glutathione.

18. A method as in claim 8, whereby before and/or during the time of exposure to sterilant, one or more of the compounds necessary for RBC reducing enzyme systems are added to the unit of RBC.

19. A method as in claim 18, wherein the concentration of the RCB reducing enzyme compound(s) is greater than its concentration in the RBC.

20. A method as in claim 13, wherein the isotonic solution is Adsol and the reducing agent is ascorbate.

\* \* \* \* \*